(12) United States Patent
Carcereri De Prati

(10) Patent No.: US 8,004,681 B2
(45) Date of Patent: Aug. 23, 2011

(54) PROCESS FOR EVALUATING THE DEGREE OF PHENOLIC RIPENESS OF A FRUIT AND RELEVANT DEVICE

(75) Inventor: Giuseppe Carcereri De Prati, Illasi (IT)

(73) Assignee: Caeleno S.R.L., Verona (IT)

( * ) Notice: Subject to any disclaimer, the term of this patent is extended or adjusted under 35 U.S.C. 154(b) by 393 days.

(21) Appl. No.: 11/918,041

(22) PCT Filed: Apr. 4, 2006

(86) PCT No.: PCT/IB2006/000780
§ 371 (c)(1),
(2), (4) Date: May 26, 2009

(87) PCT Pub. No.: WO2006/106407
PCT Pub. Date: Oct. 12, 2006

(65) Prior Publication Data
US 2010/0027011 A1 Feb. 4, 2010

(30) Foreign Application Priority Data
Apr. 6, 2005 (IT) .............................. VI2005A0098

(51) Int. Cl.
*G01N 21/00* (2006.01)

(52) U.S. Cl. ...................................................... 356/432
(58) Field of Classification Search .................. None
See application file for complete search history.

(56) References Cited

FOREIGN PATENT DOCUMENTS

| WO | WO-00/66986 A | 11/2000 |
|----|---------------|---------|
| WO | WO-01/69191 A | 9/2001 |
| WO | WO-02/077608 A | 10/2002 |
| WO | WO-2004/044558 A | 5/2004 |

OTHER PUBLICATIONS

Celotti Emilio et al., American Journal of Enology and Viticulture, vol. 55, No. 3, Jun. 30, 2004, pp. 321A.
Celotti E et al., South African Journal of Enology and Viticulture, South African Society for Enology and Viticulture, vol. 26, No. 2, 2005, pp. 75-82.

*Primary Examiner* — Gregory J Toatley
*Assistant Examiner* — Amanda H Merlino
(74) *Attorney, Agent, or Firm* — Birch, Stewart, Kolasch & Birch, LLP

(57) ABSTRACT

The invention concerns a process for evaluating the degree of phenolic ripeness of a fruit, advantageously but not exclusively grapes, that includes the measurement of the intensity of an electromagnetic wave that has passed through a portion of a skin of the fruit and an operation for correlating the intensity with a specific classification of percentages of polyphenolic substances present in the fruit.

26 Claims, 4 Drawing Sheets

PROCESS FOR EVALUATING THE DEGREE OF PHENOLIC RIPENESS OF A FRUIT AND RELEVANT DEVICE

The invention concerns a process for evaluating the degree of phenolic ripeness of a fruit, particularly suitable for evaluating the degree of ripeness of grapes, and the device suited to implement said process.

As already known, in agriculture, in order to be able to carry out effectively and at the right moment the treatments and processings necessary to obtain a high quality product it is very important to be able to know the degree of ripeness of the grown fruit timely and periodically.

This need is particularly felt in the vine-growing sector, in order to be able to obtain a good quality wine from the grapes.

This evaluation is cared out by measuring the degree of phenolic ripeness of the fruit and in paler, for red grapes, by evaluating the polyphenols (anthocyanins and tannins) present in the skin of the grape.

In this case, in fact, it is not sufficient to evaluate on the field only the sugar contents of various sample grapes, since this kind of evaluation does not supply sufficient information on the actual quality potential of the grapes, which mainly depends on the polyphenolic substances.

The processes known for the evaluation of said polyphenols in the grape skin comprise a stage in which the skins are collected and compounds are extracted, which are successively subjected to laboratory analyses.

The preparation of the sample varies according to the type of analysis required and in any case it includes the extraction of the polyphenols from the skins, an operation that is carried out in labs using suitable solvents.

If necessary, the sample obtained in this way is then purified and analysed in the laboratory.

The known analysis procedures include the evaluation of groups of compounds, like for example the total anthocyanins and total tannins, or the evaluation of the single analytes.

The applied techniques include the use of spectrophotometric, electrochemical, chromatographic systems, etc. for which costly laboratory equipment is needed.

A first drawback of the known processes for evaluating the degree of phenolic ripeness is represented by the fact that they require the use of a laboratory.

A further drawback lies in that to implement these processes the intervention of a qualified operator is needed; both for the extraction of the compounds to be analysed and for their analysis, as well as for the interpretation of the resulting data.

A further drawback lies in that in order to supply information on the accumulation of polyphenols in the skin these processes need laboratory times varying from a few hours to a few days, according to the analytical details required.

A drawback connected to the previous one is constituted by the fact that these times are not compatible with the needs of the operators of the sector.

Another drawback is represented by the fact that these evaluations cannot be made directly in the vineyard.

A further drawback lies in that to carry out this type of analyses costly equipment is required.

A further drawback lies in that to carry out this type of examinations specialised personnel and specific equipment are required.

The aim of the present invention is to overcome all the drawbacks described.

In particular, it is a first object of the invention to propose a process for evaluating the degree of phenolic ripeness of a fruit that makes it possible to measure the accumulation of polyphenols in the skin of the fruit itself and in particular of a gape.

Another object of the invention is to propose a process that can be applied directly and immediately in the vineyard or orchard.

It is a further object of the invention to propose a process that makes it possible to evaluate the actual degree of phenolic ripeness of the fruit and in particular of the grapes.

It is a further object of the invention to propose a process that makes it possible to obtain information on the actual quality potential of the grapes analysed.

It is another object of the invention to carry out a transportable device that makes it possible to evaluate the degree of phenolic ripeness of the fruit and in particular of the grapes on site and in real time.

It is a further object of the invention to carry out a device that allows the direct monitoring of the degree of phenolic ripeness of the fruit, even by the farmer, considerably reducing the need for sampling and successive laboratory analyses.

It is a further object of the invention to propose a process and a device suited to perform an objective assessment of the fruit analysed.

It is a further object of the invention to propose a process that allows a classification of grapes based on their condition before processing and transformation into wine.

It is a further aim of the invention to carry out a device that is economic and easy to use.

The aims described above are achieved through the implementation of a process and device according to the contents of the respective independent claims.

Advantageous embodiments of the invention are the subject of the dependent claims.

To advantage, the proposed device can be easily transported to the site to carry out a direct assessment of the degree of ripeness of the fruits.

Still to advantage, its simple operation allows anyone to perform an objective assessment with no need to send samples to analysis laboratories.

Still advantageously, the process and the device proposed allow the oenologist and/or vine grower to receive timely all the information useful to evaluate the quality of the grapes and of the wine that can be obtained from them.

The aims and advantages described above will be highlighted in greater detail in the description of some preferred embodiments of the invention, provided indicatively as examples without limitation, with reference to the enclosed drawings, wherein.

The process for evaluating the degree of ripeness of a fruit implemented according to the invention includes an evaluation of the percentage of polyphenolic substances, including polyphenols and anthocyanins, present in one portion of the skin of the fruit itself.

Figure 1:
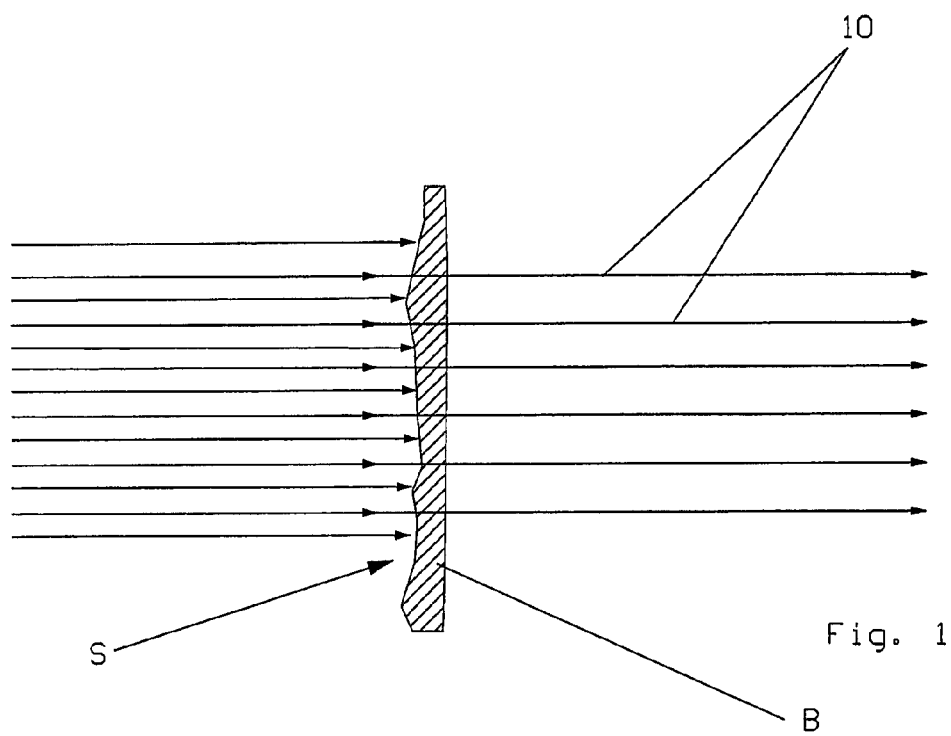
FIG. 1 is an explanatory diagram of some steps of a process subject of the invention.

In particular, according to the invention, as shown diagrammatically in FIG. 1, the process includes the measurement of the intensity of at least one electromagnetic wave 10 that has crossed at least one portion B of the skin of the fruit to be examined and an operation for correlating the measured intensity with a precise classification of percentages of polyphenolic substances present in the fruit that successively can also be associated with a corresponding degree of ripeness.

The percentage of the intensity of the electromagnetic wave measured downstream of the skin, compared to the intensity measured upstream of the skin itself, is proportional to the total polyphenols and to the anthocyanins present in the skin.

More precisely, the riper is the skin, that is, the higher is the content of polyphenolic substances, the lesser is the intensity of the electromagnetic wave.

Thanks to this correlation between intensity or luminosity (luminous intensity and/or lux watt/m$^2$) and the polyphenolic substances (tannins and anthocyanins), it is possible to evaluate the phenolic ripeness of the fruit, also directly on site and independently of the variety.

This relation, verified thanks to lab analyses carried out on portions of samples of skins of the same fruit, makes it possible to prepare in advance a diagram and/or a table and/or a data bank comprising the parameters that correlate a value of the intensity with a corresponding percentage of polyphenolic substances (anthocyanins and total polyphenols) present in the fruit, also according to the variety.

Figure 2:
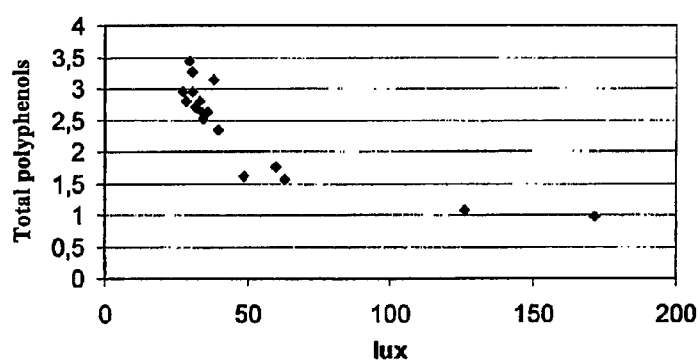
FIG. 2 is a diagram, obtained experimentally, that illustrates the correlation between the intensity of the electromagnetic wave, expressed in luminous intensity and/or lux, that can be measured with the process subject of the invention and the percentage of polyphenols present in the grape skin.
Figure 3:
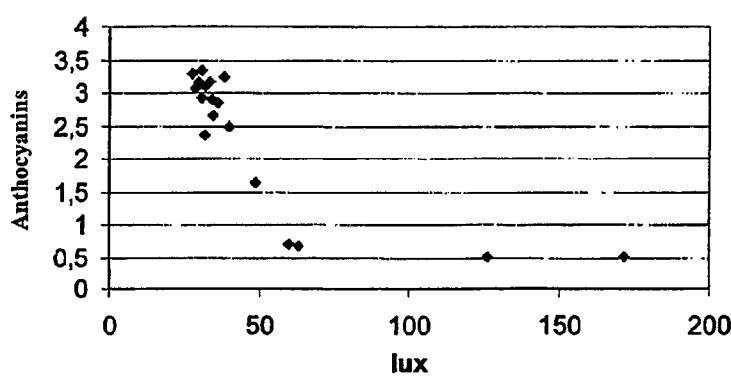
FIG. 3 is a diagram, obtained experimentally, that illustrates the correlation between the intensity of the electromagnetic wave, expressed in luminous intensity and/or lux, that can be measured with the process subject of the invention and the percentage of anthocyanins present in the grape skin.

The illustrative diagrams, obtained experimentally and shown in FIGS. 2 and 3, show the correlation between the intensity of the electromagnetic wave, expressed in luminous intensity and/or LUX and the percentage of total polyphenols and anthocyanins present in a portion of the skin of a merlot grape. Analogous correlations between the intensity measured and the characteristics of the skin can be obtained, for example, experimentally, for any other type of fruit. The same correlation also makes it possible to develop a ripeness scale suited to associate a ripeness value with a given percentage interval of the above mentioned polyphenolic substances.

Thus, transferring on a diagram and/or table and/or data bank the scale of the ripeness values obtained according to the intensity of the electromagnetic wave expressed in luminous intensity and/or LUX, it is possible to obtain a ripeness index that can be interpreted directly and is connected to precise ranges of polyphenolic substances for different fruit varieties.

For better evaluation of grapes, for example, it is advantageously preferable for the electromagnetic wave to feature a wave length included in the red area (520 nm) and in particular a frequency included between 280 and 800 nm.

Still to advantage, it is preferable that the electromagnetic wave reaches first the inner or outer surface or the double skin S of the portion B of the skin used for evaluating the degree of ripeness of the fruit.

Figure 4:
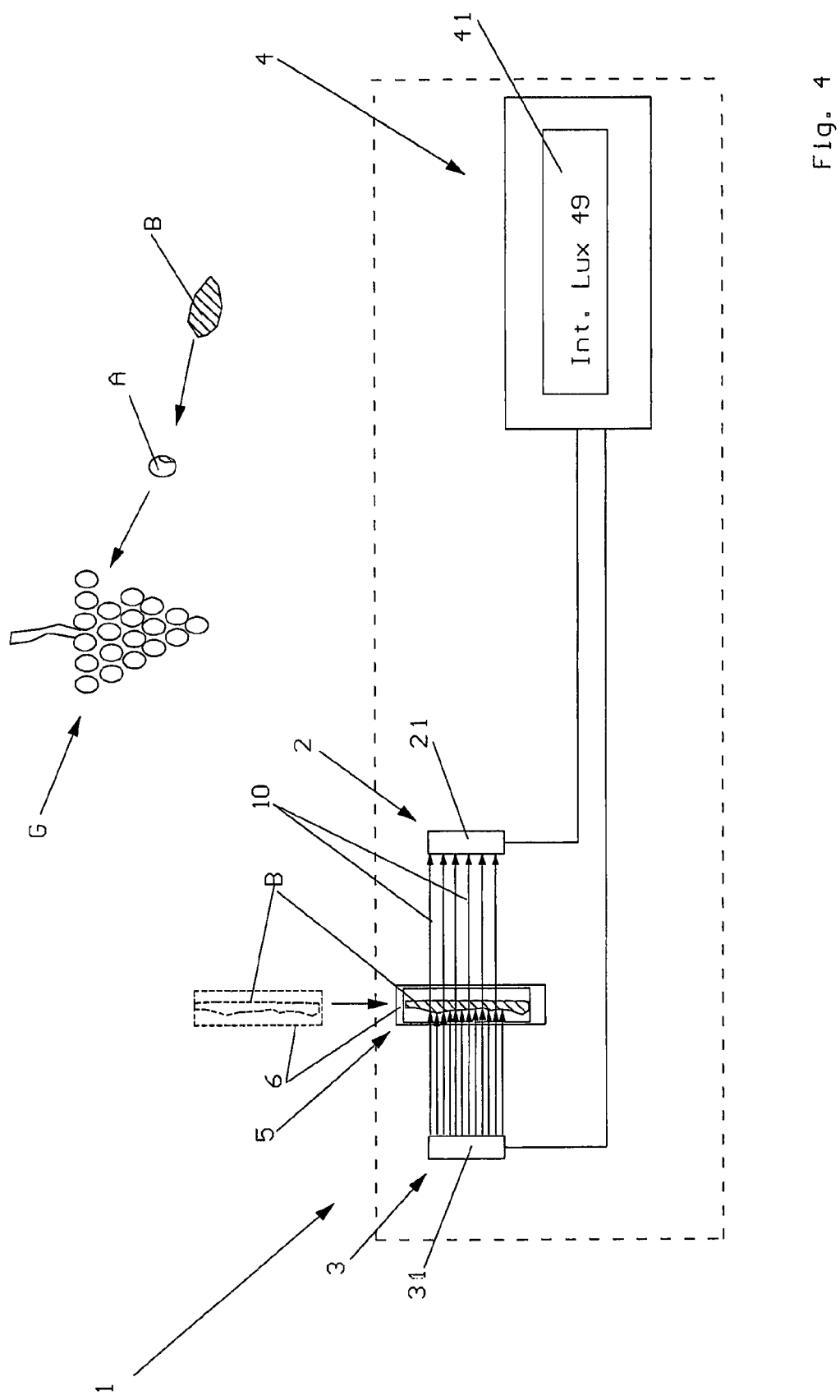
FIG. 4 shows a schematic view of a device carried out according to the invention.

A device for evaluating the degree of ripeness of a fruit that is also subject of the invention is represented in FIG. 4, where it is indicated as a whole by 1.

It comprises means 2 for measuring the intensity of at least one electromagnetic wave 10 generated by emission means 3 that has crossed a portion B of the skin of the fruit to be examined. Said measurement is supplied to the user via the signalling means 4 comprising, in the case at hand, a display unit equipped with a monitor 41.

The emission means 3 are of the monochromatic type and comprise at least one properly fed led 31 whose emission frequency is preferably included between 280 and 800 nm.

As regards the measuring means 2, they detect a frequency range included between 280 and 800 nm and comprise, preferably, at least a photodiode 21.

It should also be observed that the device is provided with a housing 5 for a removable cell 6 suited to contain/hold the portion of skin B during evaluation and transparent to the frequencies of the electromagnetic wave 10.

Another construction variant of the device subject of the invention, not represented herein, differs from the previous one due to the fact that the emission means 3 do not belong to device, but are an independent unit.

Figure 5:
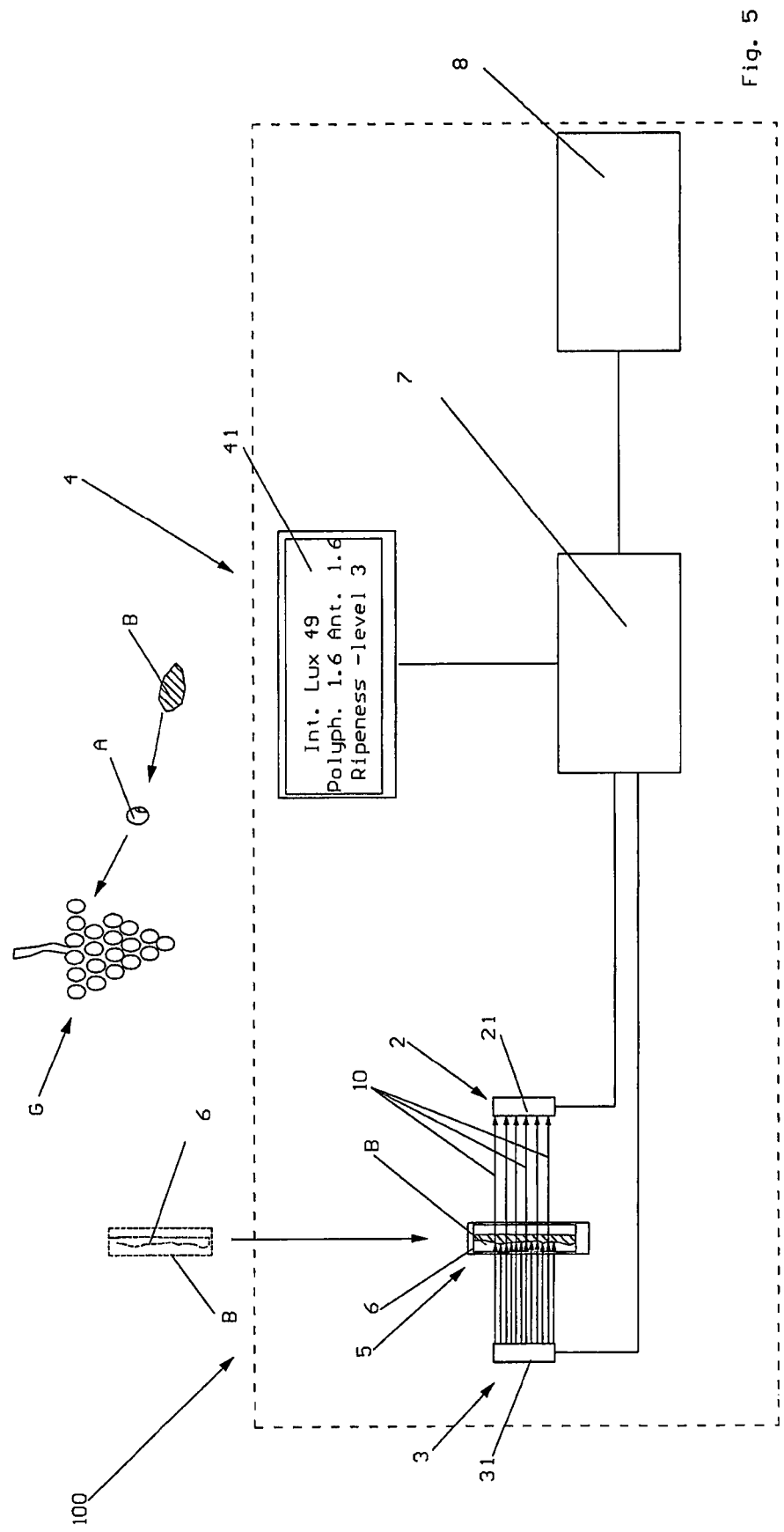
FIG. 5 shows a schematic view of another device carried out according to the invention.

Another embodiment of the invention, indicated as a whole by 100 in FIG. 5, differs from the previous one due to the fact that it also comprises processing means 7 cooperating with the measuring means 2 and the signalling means 4.

Said processing means 7 are suited to receive the measurement data supplied by the measuring means 2 and to compare them with the values present in a data bank stored in at least one memory unit, indicated as a wholly by 8, to identify the percentage of polyphenolic substances present on the portion of skin and/or the degree of ripeness of the fruit examined, as well as to transmit these data to the signaling means 4.

In particular, all the information defining a correlation between the intensity of the electromagnetic wave measured and the percentage of polyphenolic substances present in the fruit is previously stored in the memory unit.

The same unit 8 also contains a ripeness scale that, if previously stored, makes it possible to give the user, as will be better described below, an immediate evaluation of the degree of ripeness of the fruit examined.

It is clear that the values contained in the data bank vary depending on the fruit to be examined, as well as on the variety of fruit.

A further construction variant of the device subject of the invention, not represented herein, differs from the previous one due to the fact that it also comprises means suited to convey/direct the electromagnetic wave towards the skin, constituted for example by an optical system comprising lenses and/or optical fibres.

Figure 6:
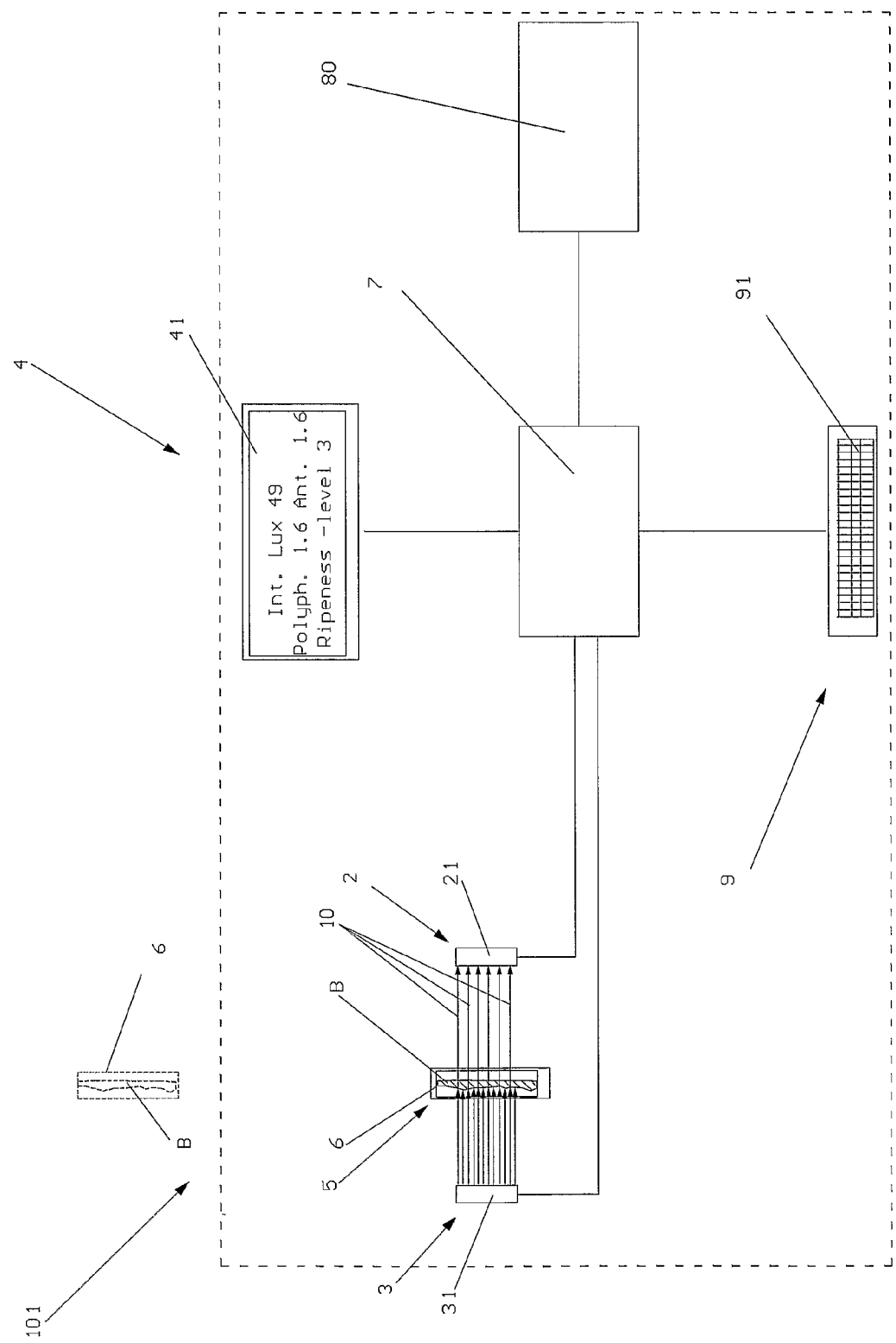
FIG. 6 shows a schematic view of a further device carried out according to the invention.

Advantageously, in a further embodiment of the invention, indicated as a whole by 101 in FIG. 6, the proposed device is equipped with a memory unit 80 containing several data banks, each one corresponding to a particular type of fruit. In this case the device is also equipped with interface means 9 suited to allow the operator to select one of the above mentioned data banks before starting the measurement.

In the case in hand, said means 9 comprise a keyboard, but, in other embodiments, they may be constituted by a button and/or a knob and/or a mouse. The operation of some of the proposed and illustrated devices, used to evaluate the degree of phenolic ripeness of a fruit, constituted, in the case in hand, by a bunch of grapes G, is described here below.

From a practical point of view the operator, to obtain the evaluation of the above mentioned degree of phenolic ripeness using the device indicated by 100 in FIG. 5, collects a grape A and simply squeezes it manually to let the must out, in order to obtain first the skin and then a portion B of the same.

Successively he/she places said portion B on the measurement cell 6 and inserts it in the apposite housing 5, directing its inner or outer part or the double skin S towards the led 31.

Finally, he/she starts the measuring procedure that includes the switching on of the led 31 and the generation, by the photodiode 21, of an electric signal proportional to the intensity of the electromagnetic wave that passes through the skin B.

The electric signal generated in this way is processed by the processing unit 7 that finds out, by comparison with the values stored in the memory unit 8, both the percentage of polyphenolic substances present in the fruit and the degree of ripeness of the grapes.

To obtain the same evaluation with the device indicated by 1 in FIG. 4, the operator instead must read on the display unit 4 the value of the intensity of the electromagnetic wave that crosses the skin B measured by the photodiode 21 and then refer to the tables or diagrams of the type shown in FIGS. 2 and 3 that correlate said value with the percentage of polyphenols and anthocyanins present in the skin.

Successively, by refining to the table or diagram that correlates such values with a ripeness scale, the operator finds the degree of ripeness of the fruit examined.

In this regard it is important to remember, as already pointed out and concerning grapes in particular, that lower values of luminous intensity and/or lux mean that the grapes are riper in terms of polyphenols, that is, have a higher polyphenol content.

It should also be observed that by making periodic measurements of the percentages of phenolic substances it is possible to transfer the measured values onto a diagram and to record the trend of said concentrations over time. This makes it possible to identify the moment of maximum concentration of said substances, which coincides with the above mentioned phenolic ripeness.

The above description clearly shows that the solutions proposed allow the set goals to be achieved.

In particular, the solution proposed advantageously allows the times and costs required by the analysis to be reduced.

The process and device proposed, although particularly advantageous for evaluating the degree of ripeness of grapes, can be used to evaluate the degree of ripeness of any type of fruit.

Still to advantage, the characteristics and the reduced dimensions of the proposed device, as well as its simplicity of use, allow the degree of ripeness of the fruit to be evaluated directly on site, even by the farmer.

Even though the invention has been described making reference to the attached drawings, upon implementation changes can be made that shall all be considered protected by the present patent provided that they are within the scope of the inventive concept expressed in the following claims.

The invention claimed is:

1. Process for evaluating the degree of phenolic ripeness of a fruit, said process comprising exposing at least one portion (B) of exclusively the skin of said fruit to at least one electromagnetic wave, measuring the intensity of said at least one electromagnetic wave (10) once it has passed through said at least one portion (B) of said skin of said fruit and an operation for correlating said intensity with a specific classification of percentages of polyphenolic substances present in said fruit.

2. Process according to claim 1), characterized in that it comprises also an operation for correlating said intensity measured and/or said percentages of polyphenolic substances with a corresponding degree of ripeness of said fruit.

3. Process according to claim 1), characterized in that it comprises the following operations:

generating a signal proportional to said intensity of said at least one electromagnetic wave (10) that has passed through said at least one portion (B) of said skin;

processing the received signal through a processing unit (7) in order to identify said percentage of polyphenolic substances.

4. Process according to claim 1), characterized in that it also includes a previous operation for creating a data bank including the parameters that correlate the value of said intensity with the percentage of said polyphenolic substances in said at least one portion (B) of said skin.

5. Process according to claim 1), characterized in that it also comprises a previous operation for developing a ripeness scale suited to associate a ripeness value with a given percentage interval of said polyphenolic substances.

6. Process according to claim 1), characterized in that said at least one electromagnetic wave has a frequency included in the red range.

7. Process according to claim 6), characterized in that said at least one electromagnetic wave has a wave length included between 280 and 800 nm.

8. Process according to claim 1), characterized in that it involves the removal from said fruit of said at least one portion (B) of said skin.

9. Process according to claim 1), characterized in that said at least one electromagnetic wave reaches first the inner or outer surface or the double skin of said at least one portion of said skin.

10. Process according to claim 1), characterized in that said polyphenolic substances comprise polyphenols and/or anthocyanins.

11. Device (1, 100, 101) for evaluating the degree of phenolic ripeness of a fruit, according to a process as claimed in claim 1), comprising measuring means (2) for measuring the intensity of at least one electromagnetic wave that has passed through at least one portion (B) of exclusively the skin of said fruit, and processing means cooperating with said measuring means (2) and suited to correlate said intensity as measured with a specific classification of percentages of polyphenolic substance present in said fruit in order to find the degree of ripeness of said fruit.

12. Device according to claim 11), characterized in that said measuring means (2) comprise means for signalling (4) the value of said intensity.

13. Device according to claim 12), characterized in that said processing means comprise at least one memory unit (8, 80).

14. Device according to claims 12) characterized in that said processing means (7) cooperate with said signalling means (4).

15. Device according to claim 12, characterized in that said signalling means (4) comprise at least one display unit.

16. Device according to claim 11), characterized in that said measuring means (2) detect a wave length included between 280 and 800 nm.

17. Device according to claim 11), characterized in that it also comprises emission means (3) for emitting said at least one electromagnetic wave.

18. Device according to claim 17), characterized in that said emission means (3) are of the monochromatic type.

19. Device according to claim 17), characterized in that said emission means (3) comprise at least one LED.

20. Device according to claim 11), characterized in that it also comprises means suited to direct said at least one electromagnetic wave towards said at least one portion (B) of said skin.

21. Device according to claim 17), characterized in that said at least one electromagnetic wave has a wave length included between 280 and 800 nm.

22. Device according to claim 11), characterized in that said measuring means (2) comprise at least one photodiode.

23. Device according to claim 11), characterized in that it also comprises at least one cell suited to hold said at least one portion (B) of said skin during said evaluation.

24. Device according to claim 23), characterized in that said cell is positioned between said measuring means (2) and said emission means (3).

25. Device according to claim 11), characterized in that it also comprises interface means.

26. Device according to claim 25), characterized in that said interface means (9) comprise at least one keyboard and/or at least one button and/or at least one knob and/or one mouse.

\* \* \* \* \*